(12) United States Patent
Hufford et al.

(10) Patent No.: US 12,283,062 B2
(45) Date of Patent: Apr. 22, 2025

(54) METHOD AND SYSTEM FOR PROVIDING SURGICAL SITE MEASUREMENT

(71) Applicant: Asensus Surgical US, Inc., Durham, NC (US)

(72) Inventors: Kevin Andrew Hufford, Cary, NC (US); Tal Nir, Haifa (IL); Lior Alpert, Haifa (IL); Gal Wiezman, Haifa (IL); Alexander John Maret, Apex, NC (US); Mohan Nathan, Raleigh, NC (US)

(73) Assignees: Asensus Surgical US, Inc., Durham, NC (US); Asensus Surgical Europe S.àR.L., Bertrange (LU)

( * ) Notice: Subject to any disclaimer, the term of this patent is extended or adjusted under 35 U.S.C. 154(b) by 373 days.

(21) Appl. No.: 17/099,761

(22) Filed: Nov. 16, 2020

(65) Prior Publication Data

US 2021/0256719 A1    Aug. 19, 2021

Related U.S. Application Data

(60) Provisional application No. 63/088,409, filed on Oct. 6, 2020, provisional application No. 62/935,585, filed on Nov. 14, 2019.

(51) Int. Cl.
*G06T 7/529* (2017.01)
*A61B 90/00* (2016.01)
(Continued)

(52) U.S. Cl.
CPC .............. *G06T 7/529* (2017.01); *A61B 90/06* (2016.02); *A61B 90/361* (2016.02); *A61B 90/37* (2016.02); *G06T 7/0012* (2013.01);

*G06T 7/70* (2017.01); *G06T 11/00* (2013.01); *A61B 2090/061* (2016.02); *A61B 2090/364* (2016.02);
(Continued)

(58) Field of Classification Search
None
See application file for complete search history.

(56) References Cited

U.S. PATENT DOCUMENTS 8,473,031 B2    6/2013 Nixon et al.
8,792,963 B2    7/2014 Zhao et al.
(Continued)

FOREIGN PATENT DOCUMENTS

| JP | 2012-529970 A | 11/2012 | |
| WO | 2009045827 A2 | 4/2009 | |
| WO | WO-2010147729 A1 * | 12/2010 | ............. A61B 34/30 |

OTHER PUBLICATIONS

PCT, International Search Report and Written Opinion from International App. No. PCT/US2020/60802 (Apr. 23, 2021).
(Continued)

*Primary Examiner* — Soo Shin

(57) ABSTRACT

A system for measuring distances within a surgical site includes a camera positionable to capture 3D image data corresponding to a treatment site. Using the image data, the system determines the relative 3D positions of identified measurement points at the treatment site captured in the images, and it estimates or determines the distance between the measurement points. Output is generated communicating the measured distances to the user. The measurement taken follows the 3D topography of the tissue positioned between the measurement points.

13 Claims, 9 Drawing Sheets

(51) Int. Cl.
 *G06T 7/00* (2017.01)
 *G06T 7/70* (2017.01)
 *G06T 11/00* (2006.01)

(52) U.S. Cl.
 CPC ........... *G06T 2207/20092* (2013.01); *G06T 2207/30004* (2013.01)

(56) References Cited

U.S. PATENT DOCUMENTS

| | | | |
|---|---|---|---|
| 9,155,592 | B2 | 10/2015 | Itkowitz et al. |
| 9,375,844 | B2 | 6/2016 | Itkowitz et al. |
| 9,492,240 | B2 | 11/2016 | Itkowitz et al. |
| 9,599,461 | B2 | 3/2017 | Gerlach et al. |
| 9,691,162 | B2 | 6/2017 | Christiansen |
| 9,987,751 | B2 | 6/2018 | Itkowitz et al. |
| 10,307,209 | B1 | 6/2019 | Yu |
| 2004/0022418 | A1 | 2/2004 | Oota |
| 2007/0038080 | A1 | 2/2007 | Salisbury, Jr. et al. |
| 2007/0167702 | A1 | 7/2007 | Hasser et al. |
| 2009/0171184 | A1* | 7/2009 | Jenkins .............. A61B 34/10 606/130 |
| 2009/0171371 | A1 | 7/2009 | Nixon et al. |
| 2010/0317965 | A1* | 12/2010 | Itkowitz ............ A61B 1/00194 382/128 |
| 2011/0188726 | A1 | 8/2011 | Nathaniel et al. |
| 2016/0070436 | A1* | 3/2016 | Thomas ............... G06T 7/0012 715/771 |
| 2016/0275703 | A1 | 9/2016 | Mariampillai et al. |
| 2017/0172382 | A1* | 6/2017 | Nir ........................ A61B 1/05 |
| 2017/0188011 | A1 | 6/2017 | Panescu et al. |
| 2018/0177561 | A1 | 6/2018 | Mintz et al. |
| 2018/0350073 | A1 | 12/2018 | Shokri et al. |
| 2019/0108396 | A1* | 4/2019 | Dal Mutto ............ G06V 20/52 |
| 2019/0201107 | A1* | 7/2019 | Hufford ............... A61B 90/361 |
| 2019/0231220 | A1 | 8/2019 | Refai et al. |
| 2019/0272634 | A1 | 9/2019 | Li et al. |
| 2019/0365252 | A1 | 12/2019 | Fernald et al. |
| 2020/0367985 | A1* | 11/2020 | Penny .................. A61B 46/00 |
| 2022/0265361 | A1* | 8/2022 | Hufford ............... A61B 17/062 |

OTHER PUBLICATIONS

Kim et al., "Computer Assisted 3D Measurements for Micro-Surgery", Proceedings of the Human Factors and Ergonomics Society 41st Annual Meeting, pp. 787-791 (1997).

Pinto, J.R. et al., "An On-Line Measuring System to Support Heart Surgery", Image Processing and its Applications, Conference Publication No. 465 IEE 1999, pp. 377-381.

Reiter et al., "Appearance learning for 3D tracking of robotic surgical tools", The International Journal of Robotics Research, vol. 33(2), pp. 342-356 (2014).

Supplementary European Search Report for European Application No. EP20886615 issued May 29, 2024.

Japanese Office action from related Japanese Patent Application No. 2022-527869 issued on Jun. 25, 2024.

\* cited by examiner

METHOD AND SYSTEM FOR PROVIDING
SURGICAL SITE MEASUREMENT

This application claims the benefit of U.S. Provisional Application No. 62/935,585, filed Nov. 14, 2019, and U.S. Provisional Application No. 63/088,409, filed Oct. 6, 2020, each of which is incorporated herein by reference.

Inventors: Kevin Andrew Hufford, Tal Nir, Lior Alpert, Gal Wiezman, Alex Maret, Mohan Nathan

BACKGROUND

Acquiring measurement data from a surgical site can be highly useful to a surgeon or other practitioner.

Size measurements within the surgical field are typically estimated by the user as s/he views the display of endoscopic images captured of the surgical site, and s/he may refer to other elements within the image to provide size cues (e.g. known diameters or feature lengths on surgical instruments) that facilitate estimation. In more complex cases, a sterile, flexible measuring "tape" may be rolled up, inserted through a trocar, unrolled in the surgical field, and manipulated using the laparoscopic instruments to make the necessary measurements.

Co-pending and commonly owned U.S. application Ser. No. 17/035,534, entitled "Method and System for Providing Real Time Surgical Site Measurements" describes a system and method that use image processing of the endoscopic view to determine sizing and measurement information for a hernia defect or other area of interest within a surgical site.

This application describes a system for providing sizing and area measurement information that is more accurate and convenient than current methods.

DETAILED DESCRIPTION

This application describes a system and method that analyzes the surgical site using computer vision, and that measures a distance or series of distances within the surgical site.

Figure 1:
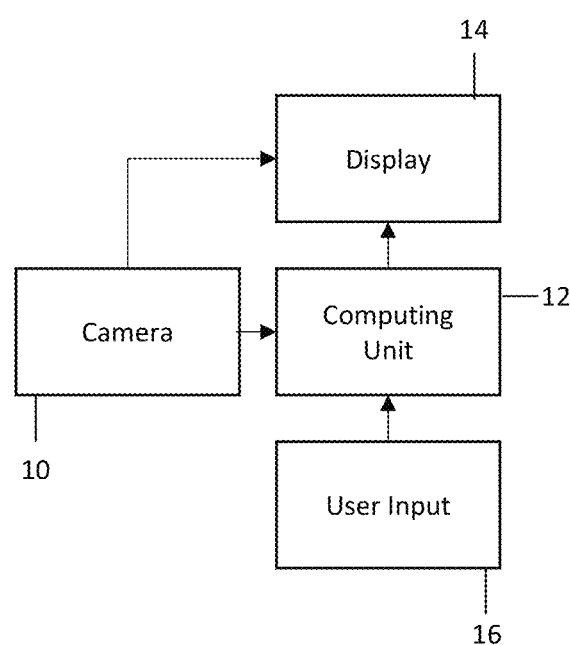
FIG. 1 is a block diagram schematically illustrating a system according to the disclosed embodiments.

Referring to FIG. 1, an exemplary system preferably includes a 3D camera 10, one or more processors 12 receiving the images/video from the camera, and a display 14. The 3D camera is preferably an endoscopic/stereoscopic camera. It may comprise a pair of cameras (stereo rig), or structured light-based camera (such as Intel RealSense™ camera), or a 2D camera using other software or hardware features that allow depth information to be determined or derived. The processor(s) includes at least one memory storing instructions executable by the processor(s) to (i) determine the 3D positions of points on the images captured by the data, (ii) based on the 3D positions, estimate or determine the straight line and/or geodesic distance in 3D between identified measurement points at the surgical site being imaged by the camera and (iii) generate output communicating the measured distances to the user. The 3D information is either processed by a processor within the camera or separate from the camera, depending on the type of the camera. The output may be in the form of graphical overlays on the image display displaying the measurement data (as described in connection with the drawings), and/or in other forms such as auditory output.

The distance measured may be the straight line "ruler distance" between the measurement points, and/or the geodesic distance between the points, which takes into account the variations in depth of the surface features (e.g. the tissue surface) along the line between the two points. Note that these measurement points are attached to the locations at the appropriate depth of the tissue or other structure within the body cavity at which a measurement is being take, (as determined using the system, rather than floating above the tissue at some point in space).

The system additionally includes a device or feature by which measurement points are identified to or by the system in a number of different ways. As one example, the user may identify the measurement points to the system using one or more user input devices 16. When included, a variety of different types of user input devices may be used alone or in combination. Examples include, but are not limited to the following devices and methods, and examples of how they might be used to identify measurement points when the system is in a measurement point input mode of operation:

Eye tracking devices. The system determines the location at which the user is looking on the display and receives that location as input instructing the system to set that location as a measurement point. In a specific implementation, when in a measurement point input mode of operation, the system displays a cursor on the display at the location being viewed by the user, and moves the cursor as the users gaze moves relative to the display. In this and the subsequently described examples, confirmatory input (discussed below) can be input to the system confirming the user's selection of a measurement point.

Head tracking devices or mouse-type devices. When the system is in a measurement point input mode of operation, the system displays a cursor on the display and moves the cursor in response to movement of the head-worn head tracking device or movement of the mouse-type of device.

Touch screen displays, which display the real time image captured by the camera. The user inputs a desired measurement point by touching the corresponding point on the displayed image.

Movement of an input handle that is also used to direct movement of a component of a surgical robotic system. Input handles may be used with the operative connection between the input handle and the robotic component temporarily suspended or clutched so the input handle moves a cursor displayed on the display.

Figure 4A:
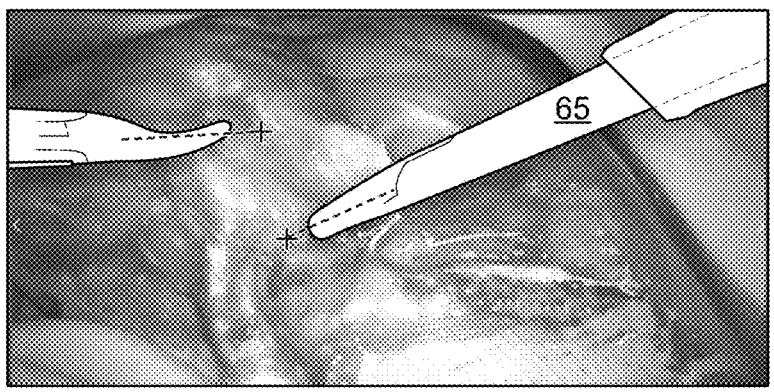
FIGS. 4A-4D shows examples of a GUI displaying an image of a surgical site and illustrates use of surgical instruments to identify measurement points to the system.
Figure 4B:
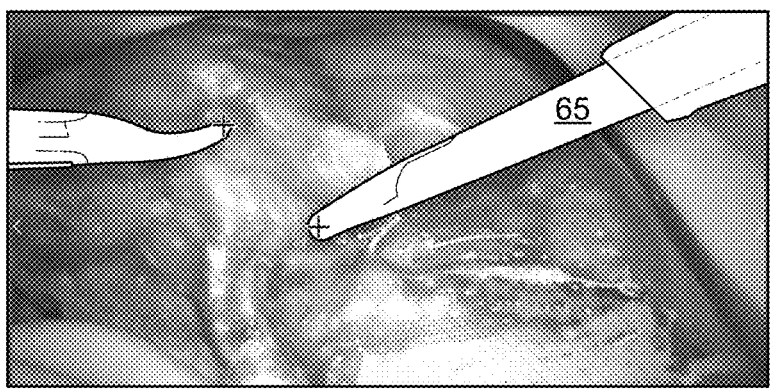
Figure 4C:
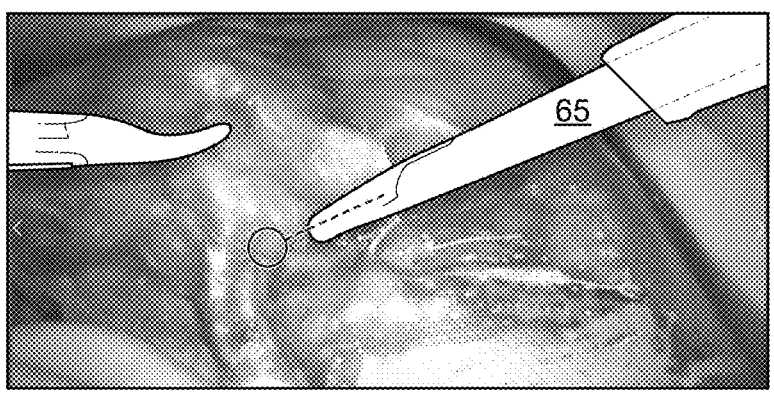

Movement of another component on the input handle for a robotic surgical system, such as a joystick, touchpad, trackpad, etc.;

Manual or robotic manipulation of a surgical instrument (with the robotic manipulation performed based on using input from an input handle, eye tracker, or other suitable input device) within the surgical field. For example, the instrument may have a tip or other part (e.g. a pivot of a jaw member, rivet, marking) that is tracked using image processing methods which the system is in an instrument-as-input mode, so that it may function as a mouse, pointer and/or stylus when moved in the imaging field, etc. The tracked part may be recognized by the system or identified to the system by the user. Alternatively or additionally, a graphical marking can be displayed on the display over (as shown in FIG. 4B) or offset (as shown in FIGS. 4A and 4C) from the instrument. These icons are moved by the user through movement of the surgical instrument (manually or by a robotic manipulator that moves the instrument in response to user input). See the discussion of FIGS. 4A-5D. Where robotically manipulated surgical instruments are used to identify measurement points to the system, the positions of the measurement points may be calculated using only the 3D image data, and/or using information derived from the kinematic data from the robotic manipulators on which the instruments are mounted.

The system may be configured or placed in a mode so that the measurement points are recognized on the image using computer vision. Such points might include points on surgical devices or instruments (e.g. tips or other structural features, or markings) recognized by the system, edges or other features of tissue structures or tissue characteristics, etc. U.S. application Ser. No. 17/035,534, entitled "Method and System for Providing Real Time Surgical Site Measurements" describes techniques that may be used for identifying structures or characteristics.

Voice input devices, switches, etc.

The input methods described above may be combined in a variety of ways. For example, the system might apply computer vision to recognize certain anatomical or tissue features, and then measure the distance between the identified feature and a graphical icon displayed over the instrument tip.

Input devices of the types listed are often used in combination with a second, confirmatory, form of input device allowing the user to enter or confirm the selection of a measurement point. If a user input for a robotic system is used, confirmatory input devices might include a switch, button, touchpad, trackpad on the user input. Other confirmatory inputs for use in robotic or non-robotic contexts include voice input devices, icons the user touches on a touch screen, foot pedal input, keyboard input, etc.

Figure 2A:
FIG. 2A shows an example of a graphical user interface (GUI) displaying an image of a surgical site. Overlays shown on the GUI display depict measurement points (marked by the overlay symbol +) between which measurements are calculated by the system, lines of measurement A and B connecting pairs of the measurement points, and measurement data representing the distance between the pairs of points.
Figure 2B:
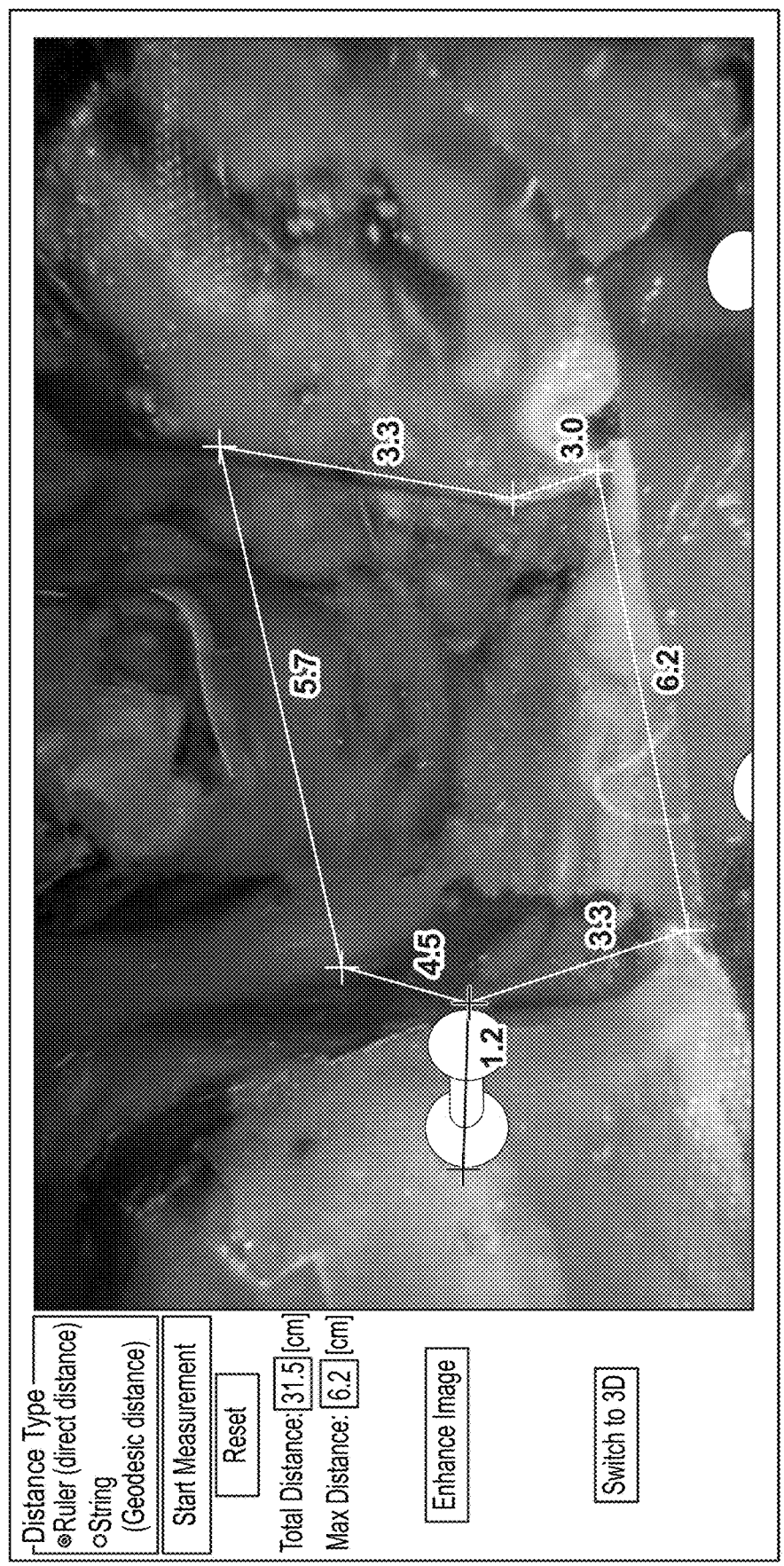
FIG. 2B is similar to FIG. 2A, and further illustrates additional lines of measurement. In some embodiments, multiple such lines may form a polygon, for which area measurements may be provided.

FIG. 2 shows an example of a graphical user interface (GUI) displaying an image of a surgical site. Overlays shown on the GUI display depict three measurement points marked using the icon "+" and between which measurements are calculated by the system. The user may instruct the system to record or place the measurement pins/way points at the desired locations using input techniques of the type described herein, and to change the location of the points in order to change the points between which measurements are to be taken. In some embodiments or modes of operation, the system might track instrument tips moving at the surgical site in real time, with measurements being continuously taken between identified points on the instruments, such as the instrument tips. Graphical markings may be generated and overlayed on the images of the instrument tips to give an enhanced visual of the points between which the measurements are being taken. This will be discussed in further detail in connection with FIGS. 4A-5B.

Overlays representing lines of measurement connecting pairs of the measurement points are also shown, together with the corresponding measurement data. The measurement may be point to point data, meaning the straight line distance between the points, or geodesic distance across the tissue surface between the measurement points. Note with respect to FIG. 2, which gives geodesic measurement distances, that some displayed lines appear to be of similar length on the GUI, but the distances measured along those lines (and numerically displayed between the lines) are greatly different due to variations in surface depth between the measurement points.

As mentioned above, in some cases it is useful to provide measurements of the actual path along the tissue rather than providing a straight-line measurement between two points. This analogy may be made between using a rigid ruler to create a measurement and placing an overlay of a string along a surface between those two points. The "string" can snap to features captured by the image data, or it can be smoothly adjusted. Both types of measurement are represented by the overlays shown in FIG. 3A, in which the geodesic measurements (identified using overlays showing irregular lines and distance data in parenthesis) and straight line measurements (identified using overlays showing straight lines and distance data outside the parenthesis). In some implementations, a weighted graph search along the surface is used to find the minimum path length between two points. In some implementations, a weighting or optimization function may be used to create a smoother path between the measured points.

Figure 3A:
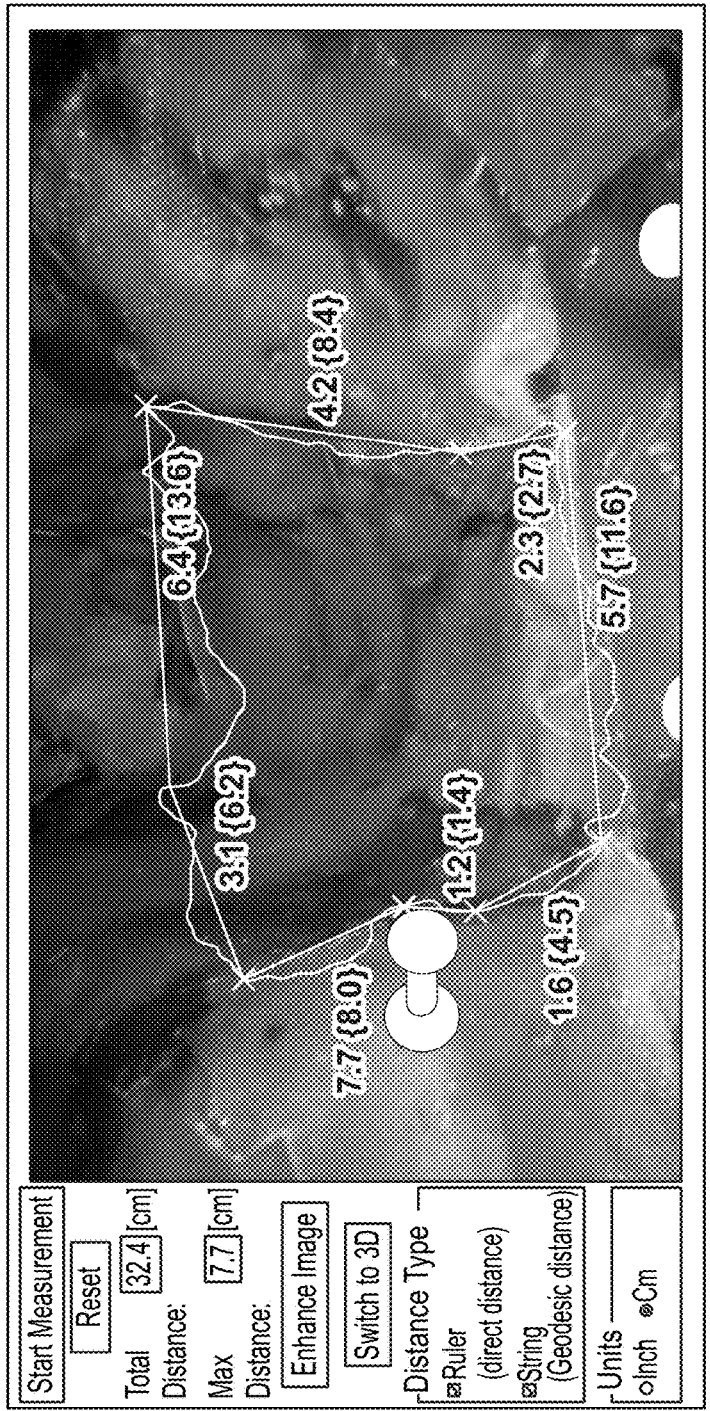
FIG. 3A is similar to FIG. 2A and further illustrates the difference between geodesic measurements (identified using irregular lines and shown parenthetically) and straight line measurements (identified by straight lines and shown outside the parenthesis).
Figure 3B:
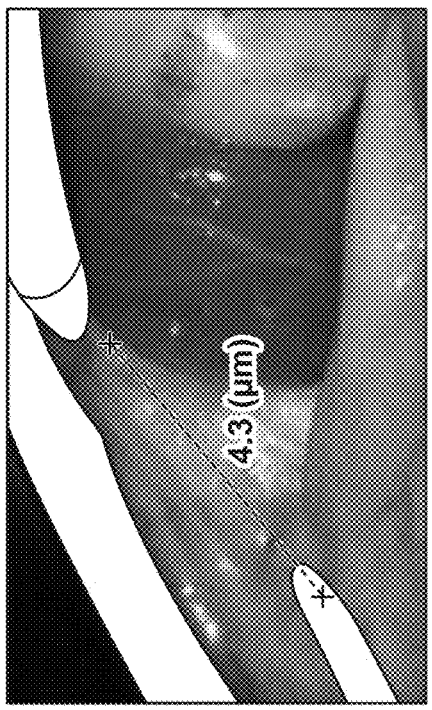
FIG. 3B shows an example of a GUI displaying an image of a surgical site, in which the measurement points + are identified using points on two surgical instruments within the surgical field.

Referring to FIG. 3A, multiple measurement points may be identified to the system, and multiple measurement lines identified that form a polygon. This allows the system to calculate area measurements if desired.

In some implementations, the geodesic distance may be measured by projecting a line between the two selected points along the view direction of the endoscope/laparoscope onto the surface, and measuring its resultant path length.

Where measurement data is being generated for tracked structures (e.g. the distance between two instrument tips in the field, or between an instrument tip and a marked or computer-recognized feature of the surgical site), the measurement data may dynamically update as instruments or other tracked structures move at the surgical site, and the overlay positions may move to track the movement of the tracked instruments/features.

In some displays it might be useful to provide an overlay that appears to lie on a surface/contour or series of surfaces in the endoscopic image. The overlays showing the path of the "string" measurement in FIG. 3A are examples of this. This overlay would be constructed making use of the 3D data representing surface locations at the surgical site. It may be at least partially transparent so as to not obscure the surgical field.

Other forms of overlays might include those in which the distance measurement is conveyed using a color, series of colors, a gradient of colors, a gradient of saturation of a single color, or any combination thereof. Different colors may be used to signify different ranges of distances. For instance, a distance of <1 cm may be displayed as a red bar, distances between 1 cm and 2 cm may be displayed with a yellow bar, and distances greater than 2 cm may be displayed with a green bar.

FIGS. 4A-4D illustrate some particular examples of methods for identifying measurement points to the system. In these examples, the position of a part of the surgical instrument is tracked by the system using computer vision or, in the case of robotically manipulated instruments, using computer vision and/or kinematic data from the robotic manipulator supporting the surgical instrument. In FIG. 4A, a graphical indicator is displayed on the display, positioned offset from the instrument. In FIG. 4B, the graphical indicator is instead displayed over a part of the instrument. In either case, as the user maneuvers the instruments robotically or manually at the surgical site, the graphical indicators move with the instruments as if they are fixed or tethered to one another.

Figure 5A:
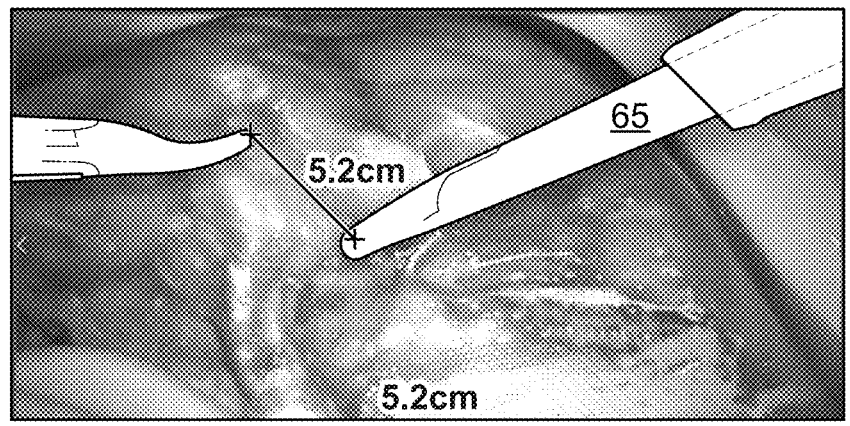
FIGS. 5A and 5B are similar to FIGS. 4A-4D, and show measurements being taken from identified measurement points.
Figure 5B:
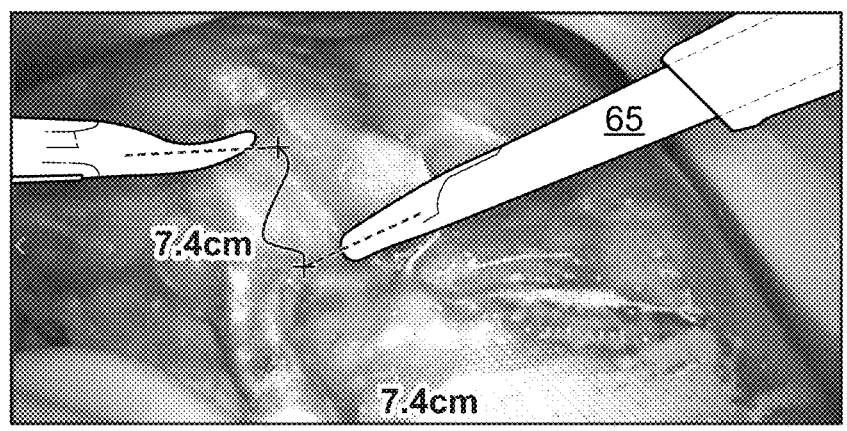

The system may be placed into a measurement mode of operation in which the measurement between the graphical indicators is continuously displayed, and thus is continuously updated as the instruments move. The path along which the measurement is taken may also be marked by a graphical indicator, with the numerical distance also displayed. In preferred embodiments, a straight line (as in FIG. 5A) is displayed if the system is taking a "ruler" measurement, and a line following surface contours of the tissue topography is shown if the system is taking a "string" measurement (FIG. 5B). Where the system offers both "ruler" measurement and "string" measurement modes, the two may be simultaneously displayed, or the user may toggle between the two using any of the types of input devices described. As one specific example, where the instruments are robotically manipulated instruments, the user may operate an input device on the user input handles used to control the robotic manipulators, so s/he can effect the toggling without removing his/her hands from the controls.

Figure 4D:
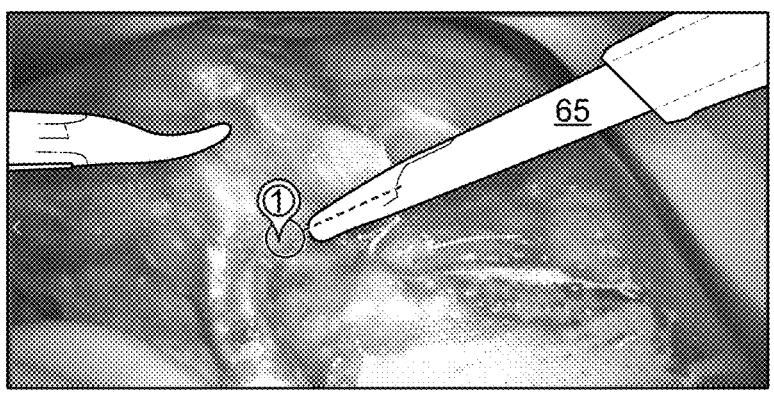

In other embodiments, at least one measurement point may be set rather than continuing to move with an instrument. FIG. 4C shows a graphical indicator that is offset from the instrument on the display and that has a circular border and a transparent interior. In this embodiment, the surgical instrument is maneuvered at the surgical site to position the graphical indicator at a location at which the user wishes to input a measurement point. Once at the desired point, the user gives input instructing the system to record that location as a measurement point. In a specific embodiment, where the instrument is a robotically manipulated one, the user may operate an input device on the user input handle to signal to the system that the location at which the graphical indicator is located is to be received as a measurement point. The system may optionally give visual confirmation of the measurement point by dropping a graphical tag at the point, as shown in FIG. 4D. Subsequent measurement points may be optionally identified in a similar manner, and then the system may be instructed to display measurements between the identified measurement points or combinations of the points. Alternatively, as instruments are moved within the surgical site, measurements between the tag and predetermined parts of instruments within the field (e.g. as marked in FIG. 4A, 4B or 4C) may be displayed in real time as the instruments are moved.

Figure 6:
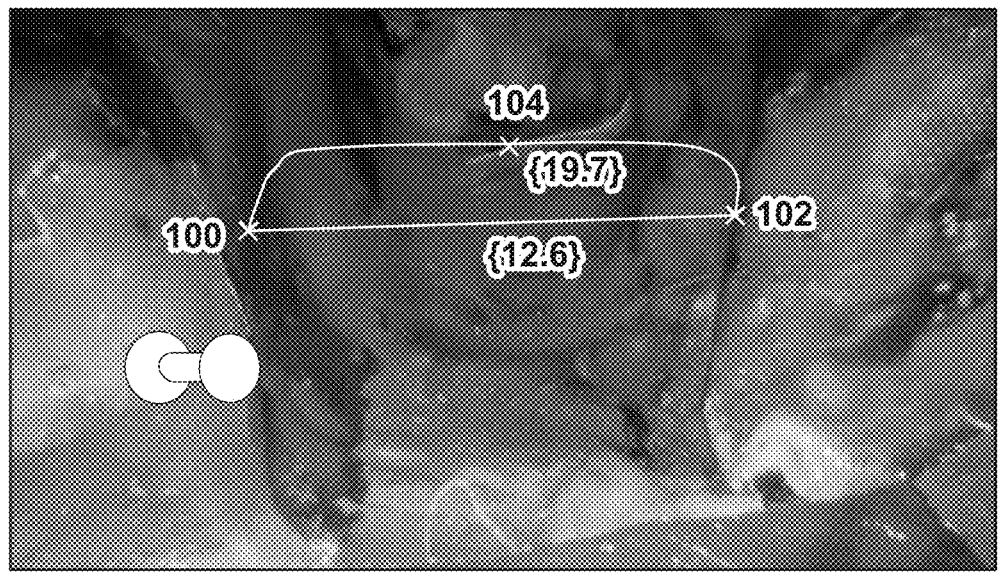
FIGS. 6-13 show a sequence of views of the display showing an embodiment in which a user defines the plane along which measurements are desired.
Figure 7:
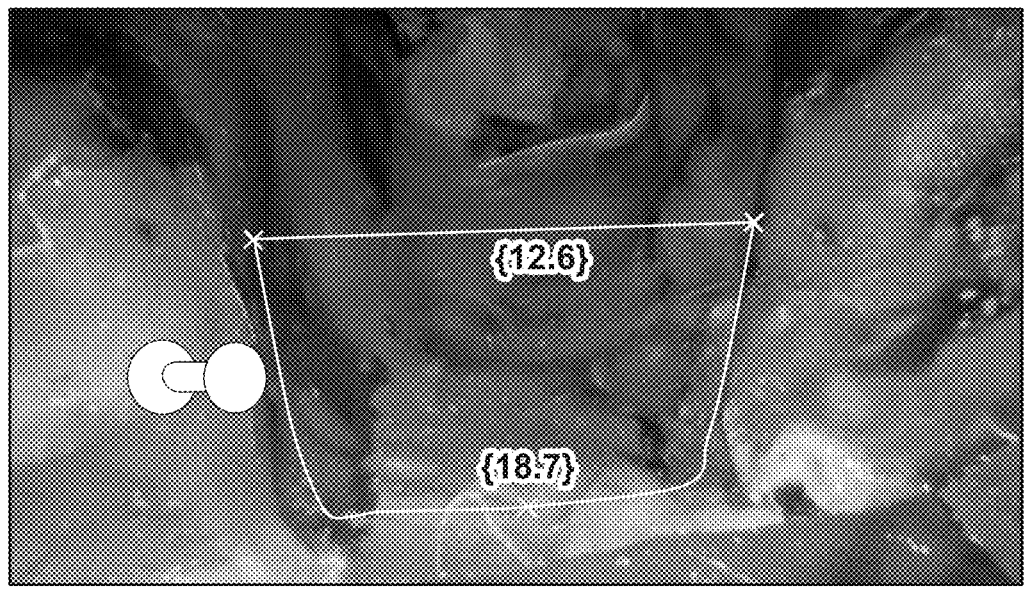

Referring to FIGS. 6 and 7, where depth measurements are to be taken, three points may be input by the user to define a plane in which the three points are located. In FIG. 6, the dimension "12.6" identifies the straight line distance between the two lateral way points 100, 102. The "19.7" dimension is the measurement between those points along the plane containing the three points 100, 102, 104, which transects the tissue surface. The user may reposition one or more of the points to obtain different measurements. In FIG. 7, the way point 104 has been moved to another location, thus defining a different plane along which the measurement is to be taken.

Figure 8:
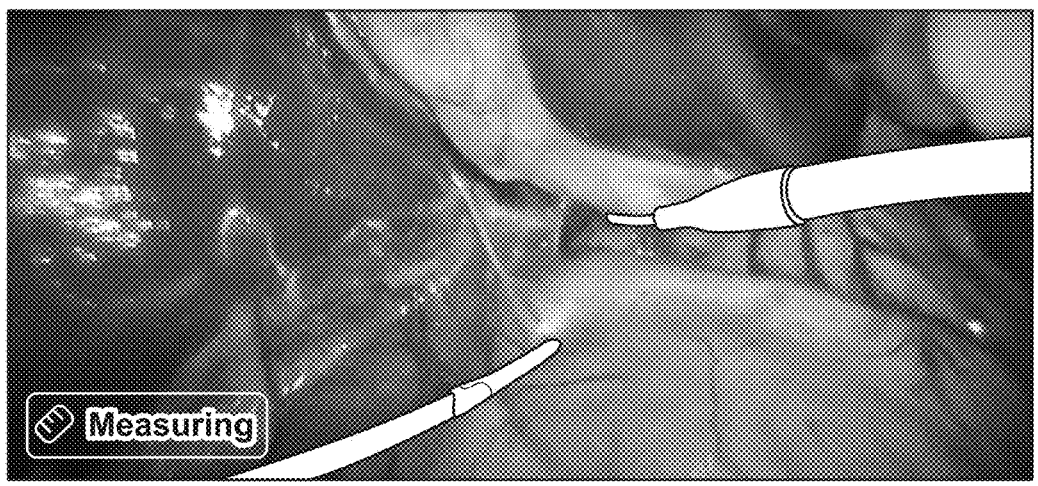
Figure 9:
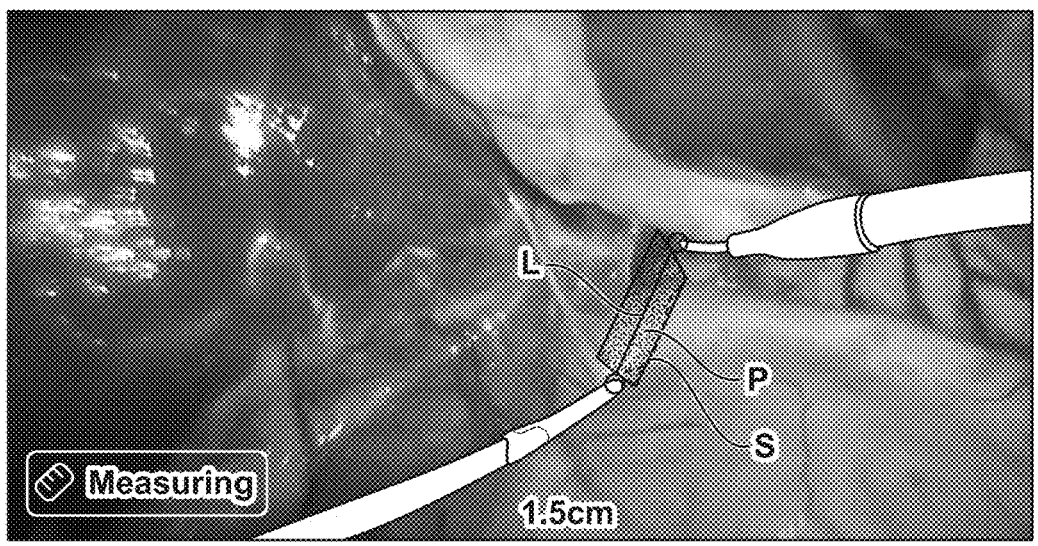
Figure 10:
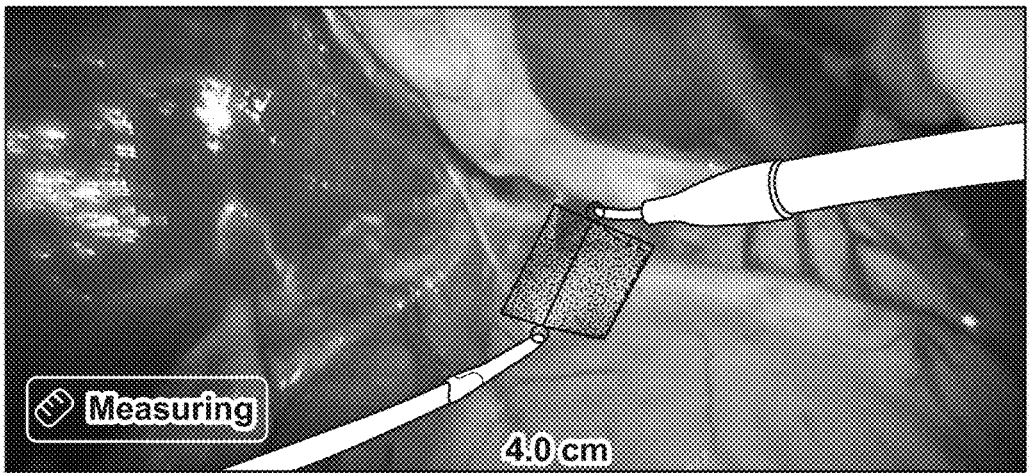
Figure 11:
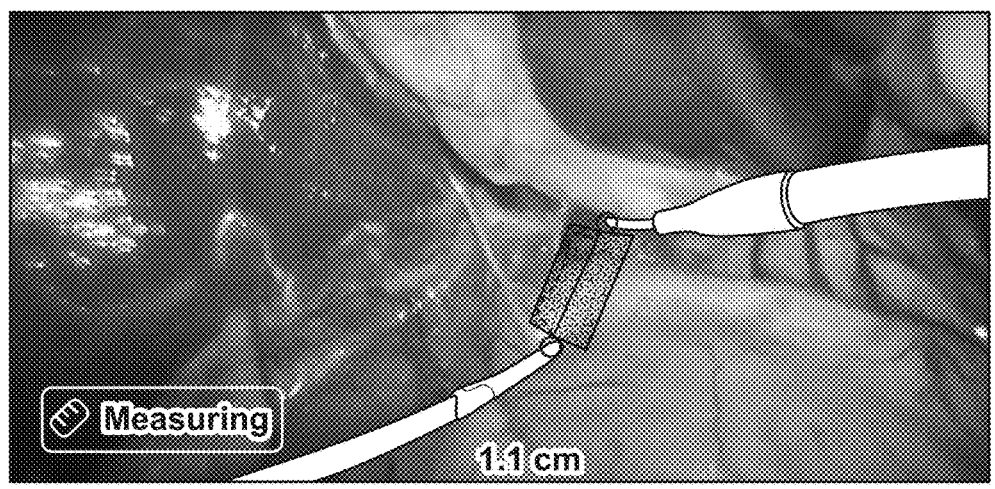
Figure 12:
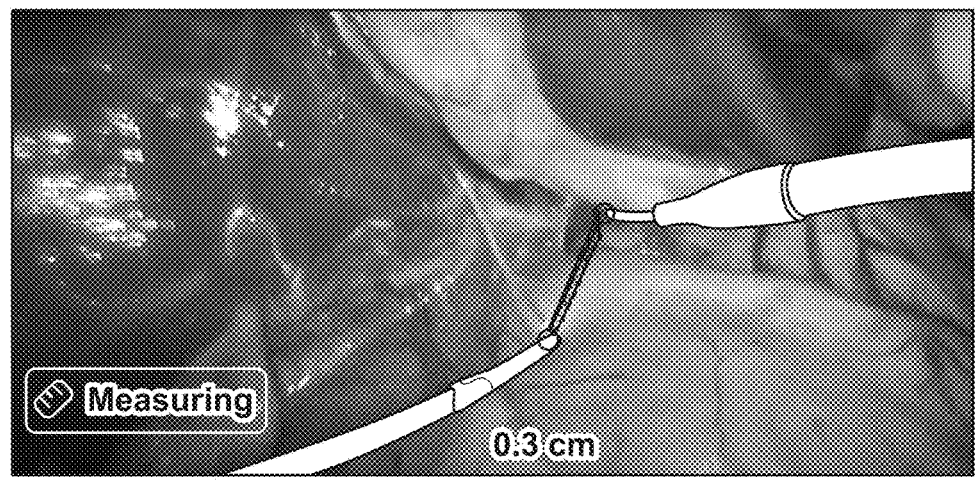
Figure 13:
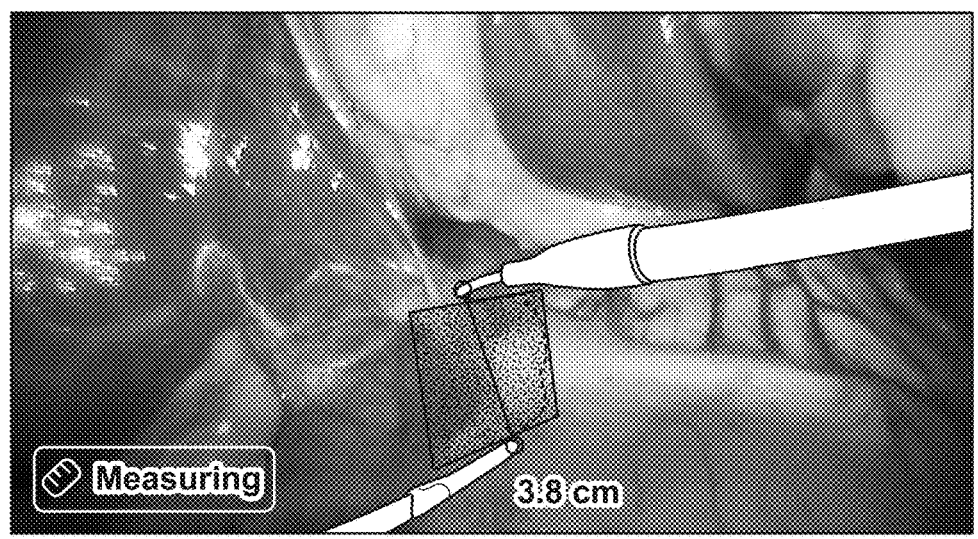

FIGS. 8-13 show a sequence of views of the display showing an embodiment in which a user may conveniently define the plane along which measurements are desired. Referring to FIG. 8, the user has positioned the tips of the instruments at locations within the surgical site. The system is placed into a measurement mode (preferably in response to user input to do so). Once in the measurement mode, the system displays a straight line L between the instrument tips (or another part of the instruments, or offset from them as described in connection with FIG. 4A). In the example shown, overlays are shown over each of the instrument tips (in this case the overlays are circular icons or targets, but they can take any form) marking the part of the instrument tip from which the measurement is being taken. An overlay of a plane P that includes the line is also displayed. The distance between the instrument tips along the plane where it transects the tissue surface is displayed at the bottom of the screen (in FIG. 9, 1.5 cm is displayed). The path of the measurement along the tissue surface S may be highlighted as shown. To reorient the plane, and to thus take the measurement along a different surface pathway between the instrument tips, the user gives an input to rotate the plane about an axis defined by the line L. Various types of user input can be given, but in one specific example a finger wheel on a user input of a robotic surgical system may be used to cause the plane to rotate about the line. FIGS. 10-12 show a sequence in which the instrument tips have not been moved, so the measurement points defining line L have remained fixed, but in which the plane P has been rotated around line L so it transects the tissue surface in different places, giving various measurement readings for the surface distance between the points. When one or both of the instrument tips is repositioned, the line is reoriented and a new plane appears, as shown in FIG. 13.

While FIGS. 12-13 show the axis defined as a straight line between instrument tips, other methods can be used to define the axis. For example, the axis may be defined by a vector perpendicular to the longitudinal axis of the laparoscope.

In some embodiments, the distances determined using the methods described here may be fed into a numerical model of features or structures. This numerical model may use a finite-element approach and use an approximated model of tissue behavior/characteristics which may be updated at each image acquisition cycle or may be updated at a higher frequency based on element properties or other predictive techniques. This model maybe used for a variety of purposes, including, but not limited to, avoiding tissue damage, moving along structures, and moving along anatomical features.

All prior patents and patent applications referred to herein, including for purposes of priority, are incorporated herein by reference.

We claim:

1. A system for measuring distances within a surgical site, comprising:
   a camera positionable in a body cavity to capture real time 3D images corresponding to a treatment site, the treatment site including a tissue surface having a topography;
   a display configured to display the real time 3D images in real time with the tissue surface and topography visible on the display;
   at least one processor and at least one memory, the at least one memory storing instructions executable by said at least one processor to:
   identify, using computer vision analysis of the images, a predetermined portion of a first surgical instrument that is positioned in the body cavity at the treatment site and determine a 3D position of said predetermined portion of the first surgical instrument,
   display a first overlay on the display in known proximity to the predetermined part of the first surgical instrument, such that the first overlay moves on the display to track movement of the predetermined part of the first surgical instrument, wherein a 3D position of the first overlay comprises a first measurement point;
   determine a 3D position of a second measurement point in the treatment site captured in the images,
   receive, while displaying the first overlay, input from a user observing the displayed real time images in real time, the input instructing the system to display a plane containing the first measurement point and the second measurement point,
   display a graphical plane overlay over the displayed real time 3D images, the graphical plane overlay graphically representing the plane containing the first measurement point and the second measurement point, the displayed graphical plane overlay transecting the topography of the tissue surface visible on the display, and graphically depicting a measurement pathway where the plane transects the tissue surface,
   estimate or determine a distance between the first measurement point and the second measurement point along the measurement pathway, and
   generate output communicating the distance to the user.

2. The system of claim 1, wherein the distance is a geodesic distance following the topography of tissue surfaces between the first measurement point and the second measurement point.

3. The system of claim 1, wherein the output includes generating an overlay displaying the measured distances.

4. The system of claim 1, wherein:
   the processor is further configured to
      identify, using computer vision analysis of the images, a predetermined part of a second surgical instrument positioned at the treatment site and determine a 3D position of said predetermined part of the second surgical instrument,
      display a second overlay on the display in known proximity to the predetermined part of the second surgical instrument, such that the second overlay moves on the display to track movement of the predetermined part of the second surgical instrument, wherein a 3D position of the second overlay comprises the second measurement point.

5. The system of claim 4, wherein the instructions are executable by said at least one processor to:
   receive user input to rotate the graphical plane overlay along a line extending between the first measurement point and the second measurement point;
   rotate the displayed graphical plane overlay relative to the displayed real time 3D image to a rotated orientation on the display in response to the user input to rotate the graphical plane, and graphically depict a second measurement pathway on the rotated plane along the tissue surface where the graphical plane overlay in the rotated orientation transects the tissue surface; and
   estimate or determine the distance between the first measurement point and the second measurement point along the tissue surface where the graphical plane overlay in the rotated orientation transects the tissue.

6. The system of claim 1, wherein the instructions are further executable by said at least one processor to receive input from the user identifying the second measurement point using a user input device.

7. The system of claim 1, wherein the instructions are further executable by said at least one processor to identify the second measurement point using computer vision.

8. The system of claim 1, wherein the first measurement point is on or a predetermined distance from the predetermined part of the surgical instrument disposed at the treatment site.

9. The system of claim 8, wherein the first measurement point is a point offset from a distal end of the first surgical instrument by a predetermined distance.

10. The system of claim 1, wherein the instructions are executable by said at least one processor to:
    receive user input to rotate the graphical plane overlay along a line extending between the first measurement point and the second measurement point;
    rotate the displayed graphical plane overlay relative to the displayed real time 3D image to a rotated orientation on the display in response to the user input to rotate the graphical plane, and graphically depict a second measurement pathway on the rotated plane along the tissue surface where the graphical plane overlay in the rotated orientation transects the tissue surface; and
    estimate or determine the distance between the first measurement point and the second measurement point along the tissue surface where the graphical plane overlay in the rotated orientation transects the tissue.

11. The system of claim 10, wherein the instructions are executable by said at least one processor to display an overlay showing points of transection between the graphical plane overlay and the tissue surface.

12. The system of claim 1, wherein the instructions are executable by said at least one processor to receive user input specifying a location for the second measurement point.

13. The system of claim 12, wherein the instructions are executable by said at least one processor to display a second overlay on the display at a location corresponding to the 3D location of the second measurement point.

* * * * *